(12) United States Patent
Chen et al.

(10) Patent No.: US 6,528,793 B1
(45) Date of Patent: Mar. 4, 2003

(54) ACCURATE IMAGE RECONSTRUCTION FOR DOI-PET SYSTEM

(75) Inventors: Chin-Tu Chen, Lisle, IL (US); Xiaochuan Pan, Chicago, IL (US); Chien-Min Kao, Wilmette, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/693,478

(22) Filed: Oct. 20, 2000

Related U.S. Application Data

(60) Provisional application No. 60/161,150, filed on Oct. 22, 1999.

(51) Int. Cl.$^7$ .............................................. G01T 1/164
(52) U.S. Cl. .............................. 250/363.03; 250/363.02
(58) Field of Search ....................... 250/363.03, 363.02, 250/363.07, 369, 370.09; 600/436

(56) References Cited

U.S. PATENT DOCUMENTS

| | | | |
|---|---|---|---|
| 5,323,007 A | 6/1994 | Wernick et al. ......... | 250/363.03 |
| 5,331,553 A | 7/1994 | Muehllehner et al. . | 364/413.24 |
| 5,900,636 A | 5/1999 | Nellemann et al. .... | 250/363.04 |
| 5,998,793 A | 12/1999 | Shao et al. ................. | 250/369 |
| 6,198,104 B1 | 3/2001 | Geagan et al. ......... | 250/363.04 |
| 6,232,604 B1 | 5/2001 | McDaniel et al. ...... | 250/363.03 |
| 6,239,438 B1 | 5/2001 | Schubert ................ | 250/363.03 |

OTHER PUBLICATIONS

Wernick and Chen, "Superresolved Tomography by Convex Projections and Detector Motion," pp. 1547–1553 in *Journal of the Optical Society of America*, vol. 9, No. 9, Sep. 1992.

Jeremy, "Positron Emission Tomography," pp. 15–18 in *Australian Prescription*, vol. 18, No. 1, 1995.

"Positron Emission Tomography," definition in *Dictionary of Science and Technology*, copyright 1996 by Academic Press, Inc.

Kao, et al, "Image Reconstruction for Dynamic PET Based on Low–Order Approximation and Restoration of the Sinogram," pp. 738–749 in *IEEE Transactions on Medical Imaging*, vol. 16, No. 6, Dec. 1997.

Kao, et al, "Kalman Sinogram Restoration for Fast and Accurate PET Image Reconstruction," pp. 3022–3029 in *IEEE Transactions on Nuclear Science*, vol. 45, No. 6, Dec. 1998.

*Primary Examiner*—Constantine Hannaher
*Assistant Examiner*—Otilia Gabor
(74) *Attorney, Agent, or Firm*—Welsh & Katz, Ltd.

(57) ABSTRACT

A method and apparatus are provided for reconstructing images from data obtained from scintillation events occurring within a projection space of a depth-of-interaction positron emission tomography system. The method includes the steps of identifying a segment of each depth-of-interaction detector of respective pairs of depth-of-interaction detectors detecting the scintillation-events of the data obtained within the projection space and estimating a set of sinograms from the data based upon a set of depth-independent point spread functions of the identified segments of the respective pairs of depth-of-interaction detectors.

45 Claims, 4 Drawing Sheets

—— (a) TRUE
------ (b) COMPACT+FBP
--- (c) EZPET
-·-·- (d) CONVENTIONAL+FBP

ACCURATE IMAGE RECONSTRUCTION FOR DOI-PET SYSTEM

The work described herein was performed under NIH Grant Number CA 70449.

FIELD OF THE INVENTION

The field of the invention relates to the diagnostic imaging of the human body and more particularly to positron emission tomography.

BACKGROUND OF THE INVENTION

Positron emission tomography (PET) is an invaluable, well-proven biomedical imaging modality capable of providing quantitative functional information for studying biochemical and physiological processes in vivo. Owing to its unsurpassed sensitivity, specificity, and quantitative accuracy at the molecular level, it can provide excellent diagnosis ability, staging and selection of the most effective treatment for a wide variety of cancers, heart diseases, and brain disorders. As a research tool, it is believed to be a key component in the emerging field of molecular medicine that is revolutionizing modern medicine. Finally, it can also be utilized for developing high-potency drugs at significantly reduced development cost.

To fully exploit the potentials of PET as a biomedical research tool, a notable recent trend in PET technology is the development of dedicated small-animal systems. With their small size, high resolution, and affordable cost, these systems have received great acceptance in major research institutes. It is expected that, as the size and cost of the systems continue to decrease, and their performances continue to improve, these dedicated systems may eventually become indispensable tools in biomedical research laboratories. In addition, because of the reduced system cost and design complexity, they can also serve as the test-bed of new PET technology.

Another trend in PET is the development of low-cost, high-resolution whole-body scanners for clinical use. Despite high hopes, PET has experienced a discouraging rate of growth in its initial phase of clinical applications. One major factor contributing to this disappointment is their high cost. However, PET advocates have recently demonstrated that clinical use of PET can substantially reduce medical cost by eliminating unnecessary procedures. Together with the recent FDA approval of FDG for human studies and the coverage of various PET procedures by Medicare and major health providers, PET has begun to steadily gain grounds in clinics. Even so, the use of PET is likely to be excluded from community hospitals unless its cost can be substantially reduced.

One of the major obstacles in the above-mentioned trends in PET is the presence of parallax errors resulting from events mispositioning due to gamma-ray penetration of detectors when incident at oblique angles. For ringbased systems, parallax errors have at least the following two unfavorable effects on PET: (1) they reduce image resolution and hence decrease quantification accuracy of PET and (2) the errors result in progressive degradation in image resolution as the off-center distance increases. This resolution non-uniformity can produce apparent cold spots and structural distortions, thus resulting in false diagnosis.

The practical implications of these effects are far-reaching for new-generation PET system design. For example, to provide the level of resolution (~1 mm) and sensitivity needed for imaging gene expression and transfer in animal models, long and narrow detector crystals are needed in PET. This crystal geometry is particularly susceptible to parallax errors. The microPET system developed by Cherry et al. at UCLA employs $2\times2\times10$ mm$^3$ LSO crystals arranged in a 172 mm-diameter ring. At the center of the field of view (FOV), an intrinsic resolution of 1.8 mm is obtained, but it degrades to ~2.4 mm and ~3.8 mm at 3 cm and 5 cm off the center, respectively. These figures translate into ~33% and ~111% resolution degradation at $0.35R_D$ and $0.58R_D$, respectively, where $R_D$ is the detector ring radius. For systems using BGO, crystals of 30 mm in length are often used. As a result, parallax errors in these systems are even more pronounced: a dedicated BGO small-animal system was recently reported to have ~92% resolution degradation at $0.31R_D$. Thus, PET systems of ~1 mm uniform resolution cannot be realized unless the issue of parallax errors can be resolved.

Owing to the progressive resolution degradation with the off-center distance, parallax errors also place a strong limit on the FOV radius ($R_F$) for a given $R_D$. For example, the resolution figures of the two systems described above are obtained with $R_F<0.65R_D$. For brain and whole-body PET systems, the compactness, defined as $R_F/R_D$, reported in literature are in the range of 0.5–0.6. consequently, a detector may be regarded as in coincidence with only about two-thirds of the total number of detectors in the same ring, resulting in a considerable waste of detector utilization.

Based on this observation, the CTI/Siemens ECAT ART system is able to avoid the need for almost one-third of the detectors that would be normally required (thereby substantially decreasing the product cost) by mounting two opposing detector arcs on a rotating arm. Unfortunately, this approach compromises system sensitivity since detection solid angle of the system is also reduced. Because of the importance of PET, a need exists for a better method for reducing parallax errors.

SUMMARY

A method and apparatus are provided for reconstructing images from data obtained from scintillation events occurring within a projection space of a depth-of-interaction positron emission tomography system. The method includes the steps of identifying a segment of each depth-of-interaction detector of respective pairs of depth-of-interaction detectors detecting the scintillation events of the data obtained within the projection space and estimating a set of sinograms from the data based upon a set of depth-independent point spread functions of the identified segments of the respective pairs of depth-of-interaction detectors.

DETAILED DESCRIPTION OF THE PREFERRED EMBODIMENT

Figure 1:
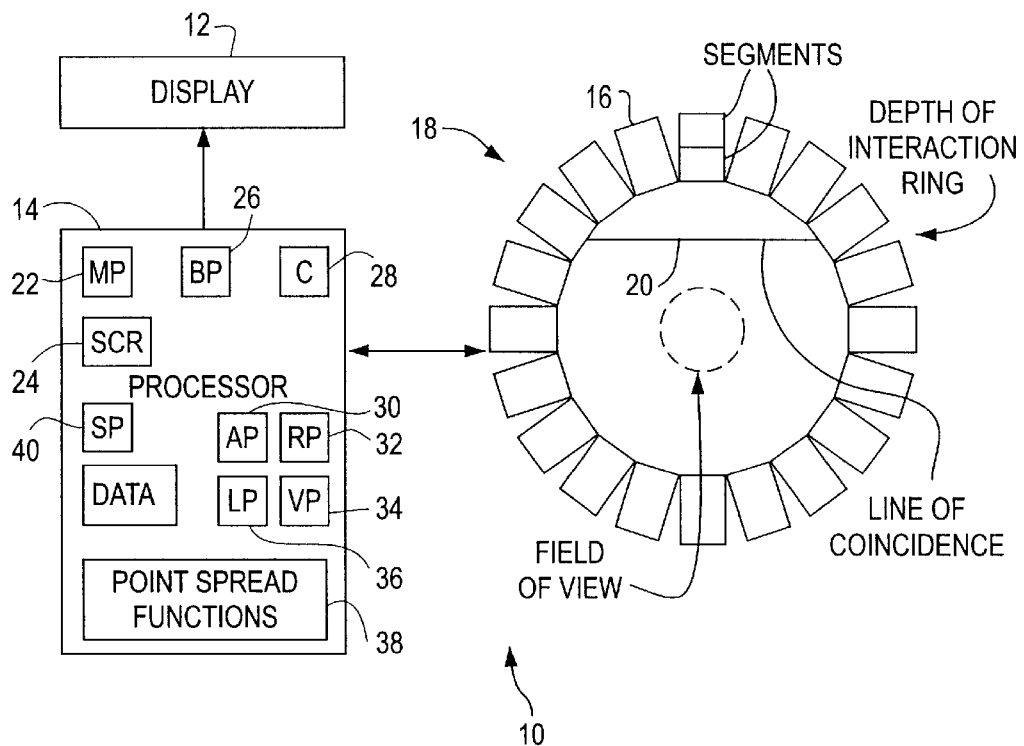
FIG. 1 is a block diagram of a DOI-PET imaging system in accordance with an illustrated embodiment of the invention.
Figure 2:
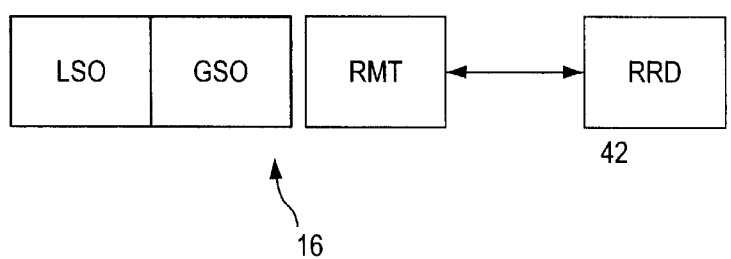
FIG. 2 depicts a DOI detector that may be used by the system of FIG. 1.
Figure 3:
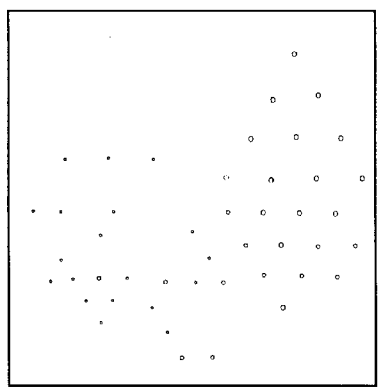
FIG. 3 depicts a Derenzo phantom panel that may be processed by the system of FIG. 1.

FIG. 1 is a block diagram of a depth of interaction (DOI) PET system 10, shown generally in accordance with an illustrated embodiment of the invention. The system 10 is unique because it uses non-iterative sinogram restoration techniques for exploiting the full information content made available by the use of the DOI detectors (and multi-modality detectors). Using this approach, the PET system 10 may use detector rings as small as the intended sizes of the field-of-view (FOV), but produce images of ultra-high resolution (1 mm) substantially free of parallax errors with no need to resort to iterative reconstruction methods.

In addition to virtually eliminating parallax errors, DOI measurement also improves the sampling of the projection space. In particular, it produces oversampling in projection space except for a small area near the center of the view (FOV). In previously reported studies, DOI-PET data have been rebinned onto a uniform grid in the projection space to form a two-dimensional (2D) matrix known as the sinogram. The filtered backprojection (FBP) algorithm is then applied to obtain a tomographic image from this sinogram. However, any image improvements achieved in this way are still limited by the parallax errors produced by the finite precision of DOI measurements.

The redundant information made available in DOI-PET data by oversampling can be exploited by signal restoration techniques described herein to correct for the parallax errors remaining in finite-precision DOI measurements. In principle, iterative reconstruction techniques could be used to obtain quantitatively accurate images if a correct model of the detection process in image space were available. However, this approach is currently often unacceptable for practical applications due to its expensive computational cost. As a result, the use of an FBP algorithm (in combination with rebinning) remains the method of choice in practice (For simplicity, we will refer to this conventional method as REBIN throughout the rest of this description).

In this description, a reconstruction method is provided for DOI PET systems, which has a good compromise between quantitative accuracy and computational speed. The method is computationally efficient enough for most practical applications while producing images with greatly improved quality in comparison with those generated by REBIN. Thus, the method developed is directed to replacing the rebinning process for producing images of improved quality from DOI-PET data on a routine basis. For applications that require optimal results, iterative image reconstruction techniques may still need to be considered when adequate computing resources are available or when long computation time can be tolerated.

In PET system design, parallax errors have prevented the use of the favorable system configuration which employs long detectors and an $R_D$ as small as the desired $R_F$. As described above, this configuration is desirable because a smaller $R_D$ requires fewer detectors and has a larger detection solid angle. A longer crystal also provides larger detection efficiency. Additional advantages of using a smaller $R_D$ include: (1) it decreases the detection angle for activities outside the axial FOV, thereby reducing the contaminations from these unwanted activities; and (2) it improves image resolution. further by reducing the point spread function (PSF) component (discussed in more detail below) contributed by photon collinearity (~1–1.5 mm for current whole-body systems). In general, parallax errors increase PET production cost and degrade its system sensitivity and spatial resolution.

As discussed above, when-using prior-art detector technology for designing high-resolution PET systems, there has been a need to sacrifice either the resolution uniformity, the detection sensitivity, or the useful FOV of the systems. To reduce parallax errors without compromising the performance, the following approaches may be incorporated into the system 10 of FIG. 1.

One method of reducing parallax errors is the development of more effective DOI detectors. Without decreasing the total detector length, these detectors can provide DOI information for positioning the coincidence lines of the detected events more accurately, thereby. reducing parallax errors without compromising the system sensitivity. Alternatively, for a desired level of resolution uniformity, DOI measurements allow the use of smaller $R_D$ for improving system sensitivity and reducing production cost. In addition, the use of DOI detectors also increase the sampling density of the projection space.

Prior-art DOI technologies proposed in literature to date can be grouped into three major categories. The first technology, called pulse height discrimination (PHD), is based on the observed difference in pulse height as the position of detection moves from the front to the back sections of the detector. When first proposed, marginal results were obtained. However, by simply segmenting the detectors 16 of the system 10, it has been found that the segment in which the detection event occurs can be unambiguously identified. Another extension of PHD technology is to collect lights at both ends of the crystal and to estimate DOI by their pulse height ratio.

In the second category, optical properties of the crystal interfaces in a block detector are engineered to modify its light sharing properties in such a way that the output produced by the traditional Anger positioning logic also conveys DOI information. This light-sharing technique has been extended to obtain multi-layer detectors capable of a very versatile depth encoding scheme.

In the above two technologies, DOI information is retrieved from the pulse amplitudes of the detected events. Since Compton scattering affects pulse amplitude, depth resolution of these technologies will be reduced by scattering as well. The third technology, known as pulse shape discrimination (PSD), involves the use of so-called phoswich detectors which consist of layers of scintillators of different light decay constants. By shape discrimination of the light decay curves, the layer in which gamma-ray interaction occurs can be unambiguously identified. This technology is almost immune to scattering and hence, in principle, can provide better depth resolution. In addition, the phoswich detectors are also very effective for building multimodality imaging systems.

Regardless of the technology used, depth resolution of DOI detectors are finite. In addition to the effect of scatter limiting and depth resolution of the first two technologies, the accuracy of depth determination is dictated by the photon counting statistics available in a scintillation event. Consequently, the depth resolution is intrinsically limited by the finite light yield of the crystal. In addition, since the light yield diminishes as the crystal size decreases, one cannot indefinitely improve the depth resolution of DOI detectors by employing decreasingly shorter crystal segments. In practice, the depth resolution is more limited by cost consideration rather than by these theoretical limits. As a result, even with the use of DOI detectors, parallax errors cannot be completely removed. The limitations imposed by the parallax errors discussed above are expected to remain, although to a lesser degree. The best depth resolution of DOI detectors reported to date is on the order of 4–5 mm.

From the perspective of image reconstruction, parallax errors are obtained because the measured PET data are not consistent with the ideal projection geometry assumed in the conventional filtered backprojection (FBP) algorithm. Therefore, another possibility for reducing the parallax errors is to employ accurate imaging models in PET reconstruction.

Often, the imaging process is characterized by a linear system of equations which relate the unknown image (spatial distribution of the radiotracer) to the sinogram (the measured PET data) in the presence of noise. In theory, the effect of finite detector resolution, and hence the parallax errors, can be removed/reduced by solving this system of equations provided that the sampling is sufficiently dense. In addition, other physical processes, such as attenuation, scatter, and randoms, can also be included in this formulation and compensated for. Many successful statistical iterative image reconstruction techniques have been developed for solving such image-space formulation (ISF); the criteria considered include maximum likelihood, maximum a posteriori distribution, maximum entropy, and minimum penalized weighted least-square errors. Algebraic iterative methods that omit explicit statistical models for the data and noise have also been investigated.

Although a considerable degree of success has been achieved, these methods typically suffer from their expensive computational cost and the issue of convergence. Consequently, they are seldom used in clinical applications. With recent phenomenal progress in computer technology, however, this situation is likely to change quickly. Even so, they are likely to be used only for off-line processing of PET data because of their iterative nature, their complexity, and the huge dimension of the system matrix involved.

The system 10 uses an approximation formulation of the imaging process completely inside the sinogram space in which the detector point spread functions (PSFs) are assumed depth independent. This sinogram-space formulation (SSF) allows the systems 10 to perform sinogram restoration (SR) for estimating the ideal sinograms, i.e., the sinograms that satisfy the ideal geometry assumed by FBP, before tomographic reconstruction. Subsequently, images of reduced parallax errors and improved resolution can be obtained by applying FBP to these sinograms. As in the case of ISF, physical factors such as attenuation, scatter, and randoms can also be considered.

The SSF decouples the original system of equations in ISF into a set of substantially smaller subsystems of equations. These subsystems are much easier to solve. Moreover, for ring-based PET systems, the matrices of these subsystems are approximately identical. As a result, it is only necessary to consider a single small system matrix in SSF. It has been observed that a given iterative method in SSF involves a considerable improvement in convergence rate and reduction in computation time per iteration, as compared to the same iterative method in ISF. On the other hand, image quality obtained by using SSF is quantitatively comparable to that obtained by using ISF. Hence, substantial savings in total computational cost can be achieved by SSF without sacrificing image quality.

A more significant advantage offered by SSF is perhaps the possibility of using non-iterative methods for accurate image reconstruction. For dedicated small-animal systems using SSF (which produce approximately 100 data samples per view), it has been found that it is practical to pre-compute and store the inverse matrix required for solving the subsystems of equations. On the other hand, for larger PET systems in which the direct inverse approach is impractical, a recursive technique has been developed based on Kalman filter. This method is capable of dealing with non-stationary PSFs and non-stationary noises. At any instant, it requires only a very small matrix for operation (on the order of 10×10). Since the method is non-iterative, it does not suffer from the issue of convergence. It can incorporate non-trivial a priori models for noise regularization. Finally, it is computationally very efficient.

The developments of DOI detectors and SR techniques provide us a converging point-for the historically separate routes of hardware (instrumentation) and software (reconstruction) developments for improving PET image quality. In this research, an integrated design concept is used for the development of high-quality, compact PET systems.

It is anticipated that the proposed new concept of system 10 provides the following benefits to PET technology. It provides an economic means for developing compact PET systems of 2 mm uniform spatial resolution and better. As discussed above, such high resolution systems are difficult to realize unless new detector technologies can be developed. These developments are usually difficult and only marginal performance gain is often achieved with substantial investment.

In addition, the small detector-ring radius also helps improve resolution by reducing the blur caused by photon non-collinearity. Due to its compactness, it can significantly increase system sensitivity to true events and decrease contaminations from activities from outside th axial FOV. The associated improvement in quantification accuracy is significant to the emerging field of molecular medicine. Since fewer detectors are needed, it also substantially reduces PET production cost. By incorporating sophisticated SR methods for compensation of the effects of nonideal geometry, a greater degree of flexibility in PET configuration can be obtained. For example, it may become practical to employ inexpensive, fast, or high light-yield scintillators of low density in PET that have been previously excluded due to considerations of parallax errors. It may also allow the use of non-conventional geometry and detector design. Such flexibility can be utilized for further PET performance improvement and cost reduction. As will be discussed in later sections, the ezPET design of the system 10 also promises user-friendliness for non-expert users.

The high-quality, low-cost, and user-friendliness nature of an ezPET system considerably facilitates the penetration of PET technology into a wide area of biomedical research as well as various health-care delivery institutions such as the community hospitals. Considering the excellent sensitivity, specificity, and quantitative accuracy of pet in providing biochemical and physiological information in vivo at the molecular level, this penetration can bring about tremendous progress in basic biomedical research and public health care that was envisioned by the pioneers of PET several decades ago, but failed to materialize due to its high cost, limited performance, and requirement of expert knowledge in imaging physics and reconstruction algorithms for effective use.

As an example, an area that can immediately benefit from such ezPET systems 10 is the study of cellular receptors. In combination with recent progress in genetics and molecular biology, the binding mechanisms, kinetics, and genetic expression of the receptor can be studied at an unprecedented level of accuracy and detail in its living environment, natural or perturbed. The knowledge thus gained is essential for the understanding of cellular communication and recognition mechanisms, and hence of immunology, neurology, oncology, and. developmental biology, to name just a few. Artificial manipulation of biological processes at cellular levels may also become possible for disease treatment. It can also help scientists to develop smart drug delivery mechanism for targeting a specific group of cells, a technique that may prove invaluable for treatment of cancers, AIDS, and brain disorders.

Under illustrated embodiments and using computer simulation study, a 2D compact system was evaluated consisting of 160 DOI detectors made of two layers of 2.25×10 mm² LSO crystals with $R_D$=57.3 mm and $R_F$=56.3 mm, respectively (a 0.98 compactness). For comparison, a "conventional" system with 240 2.25×10 mm² single-segment LSO detectors was also considered. This system simulated the microPET geometry with $R_D$=85.9 mm and $R_F$=56.3 mm (a 0.65 compactness). For both systems, given a radiotracer distribution inside the FOV, noiseless data was generated by a ray-tracing algorithm to take into account the geometrical effects of data acquisition. As a result, the PSFs that generated the simulated data were generally depth dependent. For SR, however, we assumed depth-independent PSFs. These "restoration" PSFs were computed by moving a point source along the diameter of the FOV. The sinograms generated by conventional rebinning and by SR were both 160(views)× 113 (bins). The image sizes produced by FBP from these sinograms were 113×113. Both the bin size and the pixel size were 0.996 mm.

Figure 7:
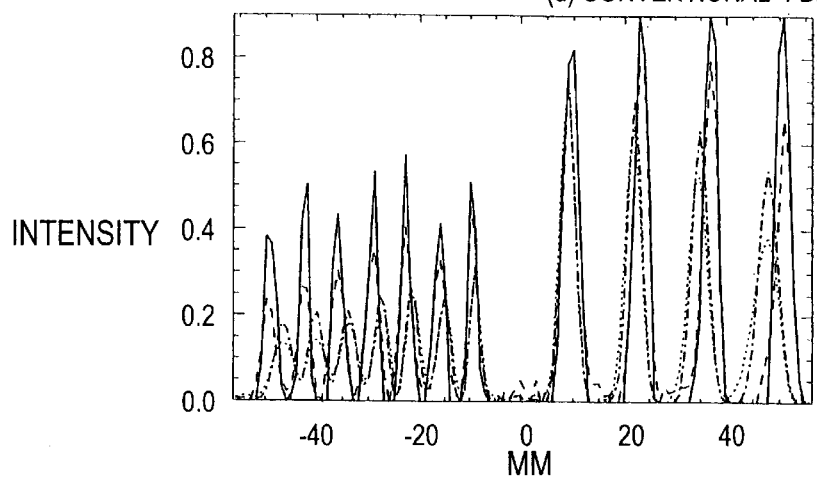
FIG. 7 depicts intensity row profiles of the Derenzo images of FIGS. 3–6.

FIGS. 3–6 compare images of the Derenzo phantom (shown as FIG. 3) (scaled to a radius equal to $R_F$) with reconstructed images obtained using the compact ring 18 (of FIG. 1) and FBP-only reconstruction (shown as FIG. 4); the compact system and SR+FBP reconstruction (shown as FIG. 5); and the conventional system and FBP-only, reconstruction (shown as FIG. 6), respectively. FIG. 7 shows example intensity row profiles of these images. The results demonstrate that, when using only FBP for image reconstruction in the compact system, as the source moves closer to the periphery, its shape becomes more radially elongated and its peak intensity decreases. In addition, its apparent position (as determined by the intensity peak) shifts inward away from its actual location. In contrast, in the ezPET image (SR+FBP image of the compact system), the source position and intensity are more accurately recovered. In addition, no significant radial elongation in shape is observed. Using the conventional system and FBP-only reconstruction, the generated image exhibits good visual quality and has small, but noticeable, resolution degradation at the periphery.

Figure 4:
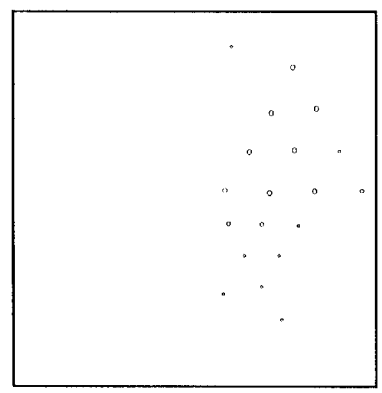
FIG. 4 depicts the Derenzo phantom panel of FIG. 3 reconstructed using data collected by the DOI ring of FIG. 1 and FBP.
Figure 5:
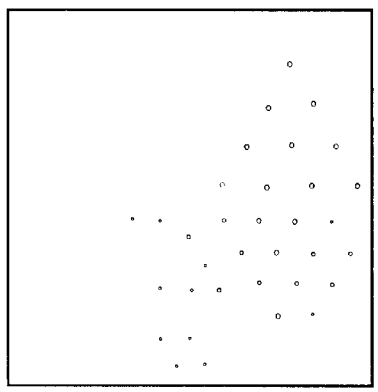
FIG. 5 depicts the Derenzo panel of FIG. 3 reconstructed using data collected from the DOI ring of FIG. 1, SR and FBP within the system of FIG. 1.
Figure 6:
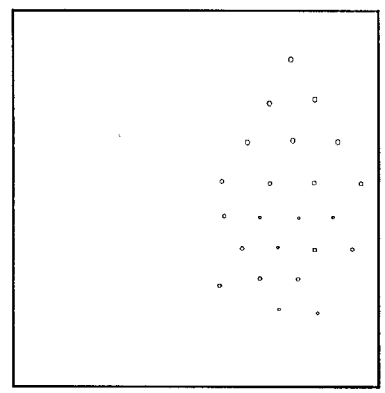
FIG. 6 depicts the Derenzo panel of FIG. 3 reconstructed using conventional methods.

However, the profile in FIG. 7 indicates that its source locations are also incorrect as in the case of FIG. 4. The results indicate that by using bilayer DOI detectors capable of a moderate depth resolution of 10 mm. and employing SR, high-quality PET images can be obtained from a system 10 with a 0.98 compactness which represents a significant improvement over the 0.65 compactness in the conventional system. It should be noted that the total detector length of the ezPET system 10 is twice as large as that of the conventional (microPET-type) system. In combination with the use of smaller $R_D$, the detection sensitivity of the compact system is estimated to be approximately 3 times that of the conventional system. This sensitivity improvement is achieved with reduced production cost (using 160 vs. 240 detectors) and excellent resolution and resolution uniformity.

PET image quality is affected by both PET instrumentation and reconstruction; only by integrating them into a seamless whole can the optimal performance be achieved. In the past, this integration was not emphasized due to expensive computational cost of accurate reconstruction methods. Moreover, it was not needed because there remained considerable room for improvement in instrumentation. As PET systems approach the theoretical performance limits, this integration will eventually become inevitable.

In a sense, the issue of parallax errors is the result of failing such an integration. As mentioned previously, in addition to reducing parallax errors, the use of DOI detectors also improves sampling of the sinogram, a situation very favorable for the application of SR. Consequently, DOI detectors and non-iterative SR techniques provide us a converging point for hardware and software developments, thus making their integration possible.

One advantage of non-iterative SR methods is that they can be implemented as hardware/firmware. For example, the inverse matrix approach discussed above for small systems requires only simple vector algebra and storage of the inverse matrix; its hardware/firmware implementation is straightforward. On the other hand, for large systems the developed Kalman-filter method may be useful. Kalman filters are well understood techniques in engineering for adaptive signal processing, controls and tracking. Their hardware/firmware implementations are mature technologies and can be found in a wide range of consumer products. As an example, they are built in cellular phone electronics for adaptive compensation of the time varying degradation typical of the wireless telecommunication channels. Hence, these non-iterative methods can be integrated with PET instrumentation at hardware/firmware level to generate the ideal sinogram on the fly. Viewed from a users' perspective, the resulting system will be free of parallax errors. We will now explore the use of this hardware/firmware implementation.

The design concept of the system 10 departs significantly from the conventional wisdom under which scientists working in the fields of instrumentation and reconstruction have labored in perfecting their respective technologies. Hence, several misunderstandings are likely to occur and the following concepts deserve special mentioning.

First, it should be emphasized that the system 10 functions to remove parallax errors rather than resolution recovery. In other words, the system 10 functions to achieve uniform resolution over the whole FOV when employing the compact configuration proposed. The system 10 does not attempt to recover resolution beyond that imposed by the detector width at image center. Consequently, a resolution constraint has been implicitly imposed during SR; hence, the difficulty associated with noise amplification often experienced in inverse problems has been greatly alleviated. Of course, when sufficient photon counts are available, the system 10 could apply the same SR techniques for achieving resolution recovery if desired. In this case, however, the system 10 may introduce detector motion or novel detector configuration in order to provide the required sampling density.

Second, the system 10 does not require the replacement of iterative image reconstruction methods with SR techniques. User-friendliness is an important key for dedicated small-animal PET systems to be received as indispensable biomedical research tools and for whole-body systems to be accepted in community hospitals because PET physics and reconstruction experts are not available at these installations. For these applications involving non-expert users, much like any consumer product, the PET systems 10 should be easy and reliable to use and their design must relieve the users of the burden of understanding its operation details. This consideration precludes the use of iterative reconstruction methods because, besides their high computational cost, they are often too complex for users to apprehend and master. In situations when iterative reconstruction are desired for producing better results, the system 10 allows users to deactivate the SR feature in ezPET systems to generate raw measured PET data.

In principle, design concept of the system 10 can be applied to any type of system geometry and DOI detector. In the system 10, a ring-based system was used with $R_F$=50 mm that employs the LSO/GSO bilayer DOI detector modules built by any number of manufacturers (e.g., CTI).

Figure 8:
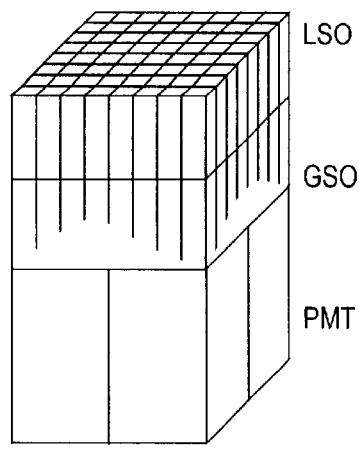
FIG. 8 depicts a perspective view of a DOI detector used by the system of FIG. 1.

For purposes of explanation, only a pair of detector modules 16 of FIG. 1 will be considered. The pair of detector modules are available from CTI (see FIG. 8). Each module has a dimension of 19×19×15 mm³ and consists of a 8×8 matrix of 2.1×2.1×15 mm³ LSO/GSO crystals, a light guide, and four photomultiplier tubes (PMTs). This detector is an excellent candidate for building high-resolution PET systems because both LSO and GSO have good light yields, fast light decays, and high densities for 511 KeV photon detection. In addition, the 20 ns difference in their light decay constants results in very good layer separation probability. The four PMT outputs are connected to a scintillation processor (SCP) 24 (e.g., PSD and Anger logic circuitry) for layer and crystal identification. Conventional PSD schemes for layer identification may be based on measuring the difference in zero cross times at the output of a shaping circuit. This scheme essentially measures the start and end times of light decay and may use a rate of rise detector (RRD) 42 to produce an output that is larger for slower decay. The PSD and the Anger logic circuitry can be implemented by using standard NIM modules. This circuitry may be interfaced with a Pentinum personal computer (PC) 14 which functions as a sinogram processor (SP) 40 for signal readouts. The PC 14 may also be used for the control of the exploratory system and off-line data processing, including data corrections, sinogram restoration, and FBP reconstruction.

Figure 9:
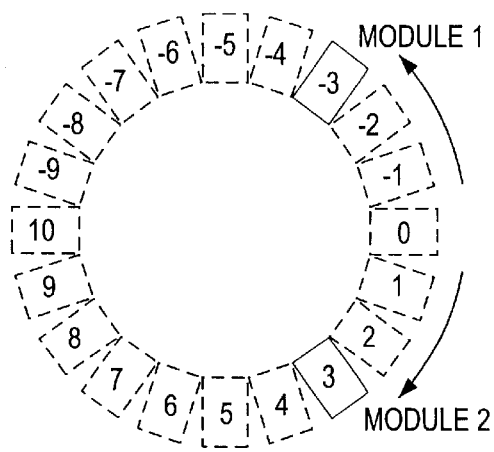
FIG. 9 depicts operation of a pair of modules that may be used in place of the ring of FIG. 1.

With only one pair of detector modules, radiotracer distributions with rotational symmetry were imaged and therefore sufficed to measure only one projection view. As shown in FIG. 9, projection can be acquired by moving the pair from ±1 position to ±9 position for simulating a system with $R_D$~57.5 mm. The required detector movement can be achieved with high accuracy with a mechanised table with a circular track that provides locking mechanism for the detector's 20 positions (see FIG. 10). The same approach can be used for systems with larger $R_D$.

Figure 10:
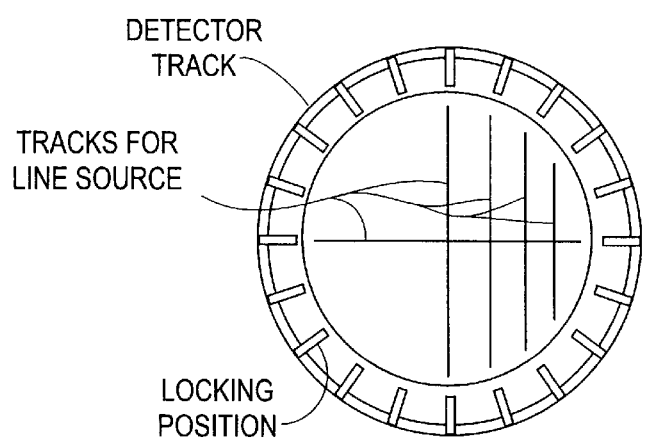
FIG. 10 depicts tracks of a line source that may be used with the FIG. 9.

PSF measurements may be considered next. As shown in FIG. 10, the table of the system 10 also provides tracks for holding line sources to measure the PSFs. Given the 2.1 mm detector width, these tracks provide good positioning accuracy so that the PSFs can be measured without significant aliasing errors. In FIG. 10, the horizontal track and the vertical tracks are designed for measuring the "restoration" PSFs and for assessing the depth dependence of PSFs, respectively. The benchtop system simulates parallax errors due to gamma-ray penetration of detectors in the same modules. Therefore, it does not simulate all geometrical effects, but this may not affect the general characteristics of the system 10. When necessary, additional LSO/GSO crystals may be placed on both sides of the detector module to provide proper attenuation and scattering.

In SSF, we have $$G_{ij}=a_{ij}h_{ij}{}^{t}x_{i}+s_{ij}+r_{ij}+v_{ij}, \quad (1)$$

where $g_{ij}$ is the jth measurement in the ith view, $X_i$=$[X_{i1}X_{i2}, \ldots, X_{iN}]^t$ is the ideal profile of the ith view and $h_{ij}$, $a_{ij}$, $s_{ij}$, $r_{ij}$, and $v_{ij}$ are the depth-independent "restoration" PSF, the attenuation factor, the scattor, the-randoms, and the Poisson noise associated with $g_{ij}$, respectively. (Note that the detector sensitivity is incorporated into $h_{ij}$.) For SR, data pre-processing is applied for corrections of $a_{ij}$, $s_{ij}$ and $r_{ij}$ to obtain $$y_i=H_ix_i+n_i, \quad (2)$$

where $y_i$=$[Y_{i1},Y_{i2}, \ldots, Y_{iM}]^t$, $y_{ij}$ is the corrected data associated with $g_{ij}$; $H_i$=$[h_{i1}{}^t, \ldots, h_{iM}{}^t]$ is the M×N system matrix with M≧N (so that SR is meaningful); and $n_i$=$[n_{i1}, n_{i2}, \ldots n_{iM}]$ with $n_{ij}$ being the noise associated with the corrected data $y_{ij}$ (no longer Poisson in general).

As in most PET systems, randoms can be corrected easily by measuring or estimating single rates. For the small system. considered, attenuation is not significant and its correction is not difficult. When necessary, it may suffice to analytically compute the attenuation factor by assuming a uniform attenuation constant; the attenuation length needed in this computation can be estimated directly from measured data. Alternatively, the attenuation factor can be measured by a transmission scan. Assuming negligible scatter and noise in the transmission scan, $t_{ij}$=$a_{ij}h_{ij}{}^t s_i$, where $t_{ij}$ is the random-corrected transmission data and $s_i$, is the known source distribution of the transmission sources. Hence, the attenuation factor can be estimated easily by $â_{ij}$=$t_{ij}/h_{ij}{}^t s_i$. (For purpose of reducing noise, $t_{ij}$ can be replaced by its smoothed value.) When applying these pre-processing for data corrections, estimates of the noise variances will be appropriately propagated in $n_i$.

For the small system considered in this research, Eq. (2) can be solved directly. Owing to the circular symmetry, we have $H_i$=$H$ independent of projection view. Without loss of generality, we can assume that $x_i$ and $n_i$ are both zero-mean random variables (otherwise, their means can be estimated and subtracted.) Consequently, the linear minimum mean-square error (MMSE) estimate of $x_i$ is given by $$\hat{x}_i=R_{x_iy_i}R_{y_i}{}^{\perp}y_i, \quad (3)$$

where $R_{uv}$=$E\{uv^t\}$ and $R_u$=$E\{uu^t\}$ for any two vectors u and v, and the superscript $\perp$ denotes the pseudo-inverse. The signal and noise are often uncorrelated; in this case, Eq. (3) becomes.

$$\hat{x}_i=R_{x_i}H^t[HR_{x_i}H^t+R_{n_i}]^{\perp}y_i, \quad (4)$$

Note that a priori information on $R_{x_i}$ and $R_{n_i}$ is required for estimating the MMSE solution. The quality of the solution is strongly affected these a priori models.

Let $e_r=[0, \ldots, 0, 1, 0, \ldots 0]^t$, where 1 is the rth element, then $$y_i = \sum_{r=1}^{M} y_{ir} e_r$$

Hence, given $y_i$ its MMSE solution is $$\hat{x}_i \sum_{j=1}^{M} y_{ir} a_{ir}$$

where $$a_{ir}=R_{x_i}H^t[HR_{x_i}H^t+R_{n_i}]^{195} e_r. \quad (5)$$

Consequently, by a careful choice of $R_{x_i}$ and $R_{n_i}$ the "inverse response functions" $a_{ir}$, j=1, ..., M, can be precomputed and the MMSE solution can be calculated within a matrix processor (MP) 22 on the fly. Obviously, by using fixed $R_{x_i}$ and $R_{n_i}$ this approach cannot produce the optimal solution for all cases. However, as already noted, the goal is to generate high-quality images for the proposed ezPET system on the fly. When optimal solutions are needed, one may use computational expensive iterative image reconstruction methods and employ an imaging model that includes as many physical processes as possible. In this description, we will investigate strategies for designing/estimating $R_{x_i}$ and $R_{n_i}$.

In this system 10, the SR may be performed off-line on the PC 14. However, the SR scheme has been specifically designed with flexibility and DSP- or ASIC-implementability in mind. For example, expert users or manufacturers can design the optimal $R_{x_i}$ and $R_{n_i}$ (empirically or heuristically) for several imaging tasks of i and pre-compute and store the "inverse response functions" $a_{ir}$. When a particular task is requested, the can download its associated $a_{ir}$'s (their lengths are expected to be short) into hardware memory of the DSP or ASIC circuitry that implement $$\hat{x}_i \sum_{j=1}^{M} y_{ir} a_{ir}$$

for estimating the ideal sinogram on-the-fly. These operations can all be implemented in a way that is transparent to non-expert users.

The system 10 has been used to explore and study the tradeoffs between various system configuration parameters. This study has consisted of the following two components. First, for given DOI detectors, the image quality has been evaluated in terms of resolution, resolution uniformity and image variance, achievable at various noise levels by SR and FBP reconstruction for various $R_D$, using a circularly symmetric resolution phantom. In particular, the image quality obtained by systems with small $R_D$ and SR reconstruction has been compared with that obtained by systems with large $R_D$ and FBP reconstruction.

Second, the issue of how image quality is affected by the DOI-detector configuration has been examined. Owing to attenuation by the front layer, measurements produced by back-layer crystals generally have fewer counts. On the other hand, a crystal has less contribution to parallax errors when located in the back layer than when in the front layer. Therefore, it may be of benefit to use shorter crystals for the front layer and longer crystals for the back-layer in order to balance the contributions to parallax errors and data noise of the two layers. This consideration is further complicated by-the use of SR due to its sensitivity to data noise, especially when performing aggressive restoration. To address this issue, the achievable image quality at various noise levels for bilayer DOI detectors with various combinations of crystal lengths have been examined.

Turning now to image reconstruction, a further example of the use of the system 10 will now be considered. For example, a DOI-PET system 10 may consist of M DOI detectors made of N segments of scintillation crystals, each of which has width w and length l. The crystal and segment within the crystal of the detector 16 in which a scintillation event occurs can be correctly identified (as described above), thus producing N possible DOI levels. The line of coincidence (LOC) for a pair of crystal segments is the line connecting the midpoints of the front faces of the two crystal segments. The LP 36 and a vector processor (VP) 34 may be used to precisely identify both the LOC and end points.

As is known, the emission of a positron within the imaged space of the ring 18 almost immediately results in collision of the positron with an electron. Collision smith an electron results in gamma-ray emission in opposites directions. The simultaneous detection of scintillation events within a pair of detectors 16 functions to identify opposite ends of the LOC. Since the distance of travel of the positron to the electron can be assumed to be a short distance, the source of the positron can be assumed to lie somewhere along the LOC.

The LP 36 and VP 34 function to identify the end points of the LOC based upon a temporal relationship of signal outputs of the DOI detectors 16. The angle $\phi$ and the position $\rho$ of the LOC defines the position of the pair in the projection space. The angle $\phi$ and the position $\rho$ are, in turn, determined by an angle processor (AP) 30, based upon the location and end points of the LOC.

The method of restoration used by the system 10 is based on the sinogram-restoration (SR) technique performed within a sinogram processor (SP) 40. This approach assumes depth-independent point spread functions (PSFs) so that we have $$E\{g_i\}=H_i p_i, \quad (6)$$

where $E\{gi\}$ is the PET data acquired in angular view i, pi is the ideal projection in the same view, and Hi is the system response matrix formed by the associated PSFs. By solving Eq. (6) within a restoration processor (RP) 32 for each view, an ideal (blur-free) sinogram can be estimated. From this restored sinogram, a tomographic image can. be obtained by FBP within a backprojection processor (BP) 26 in which the effect of blur (and hence the parallax errors) is reduced. Since the one-dimensional (1-D) signal-restoration problems in Eq. (6) can be solvced efficiently, the computational cost of this approach is small. Eq. (6) may be solved by an expectation-maximization (EM) algorithm in approximately 40 iterations; on a Pentium II 300 MHz personal computer (PC), it requires only 8.5 seconds for producing a 113×113 image from a 160×113 sinogram.

Computer simulations may be used to evaluate the performance of the SR approach. A hypothetical system with M=160 N=2 (i.e., two DOI levels), w=2.25 mm, and l=10 mm will be considered. The ring diameter of this system is 114.6 mm and its FOV is chosen to be 112.6 mm, which is 98% of the detector-ring size. The geometrical response of the system to every point in the FOV is computed by a ray-tracing algorithm. Hence, the PSFs that generate the data are generally depth dependent. For SR, however, we assume depth-independent PSFs. These "restoration" PSFs (together with the detection sensitivity required for the normalization step in rebinning) are obtained by moving a point source midway through the detector pairs. The sinograms are 160(views)×113(bins) and the images are 113×113. Both bin and pixel size are 1.0 mm.

This hypothetical system produces four sets of data, two of which are acquired by crystal pairs at the same DOI levels. For these two sets, the detection geometry is similar to that of non-DOI PET systems, and Eq. (6) provides a good approximation. The other two sets are acquired by crystal pairs at diffferent DOI levels, and their PSFs generally are depth dependent. To make use of these latter two sets, we sum the data acquired by crystal pairs in the same detector pair, thus forming a new set that would be obtained by a non-DOI PET system with 20 mm long crystals. Depth independence of the,PSFs for the three "non-DOI" data sets may be verified numerically.

Figure 11:
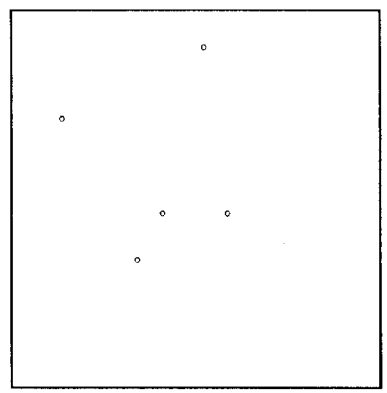
FIG. 11 depicts a conventional REBIN image.
Figure 12:
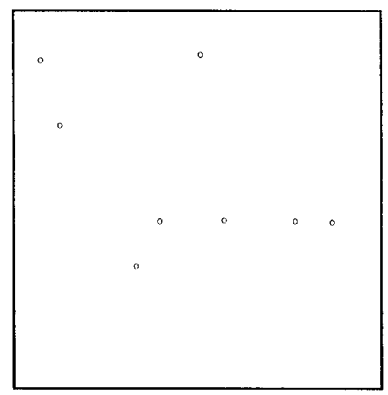
FIG. 12 depicts a true image of FIG. 11.
Figure 13:
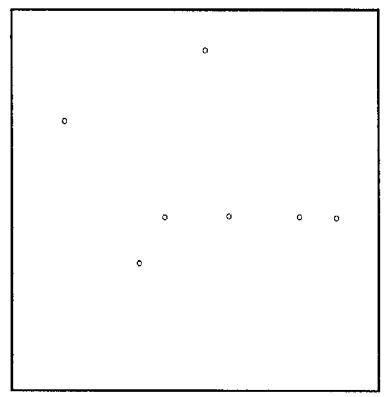
FIG. 13 depicts the true image of FIG. 12 reconstructed using SR.
Figure 14:
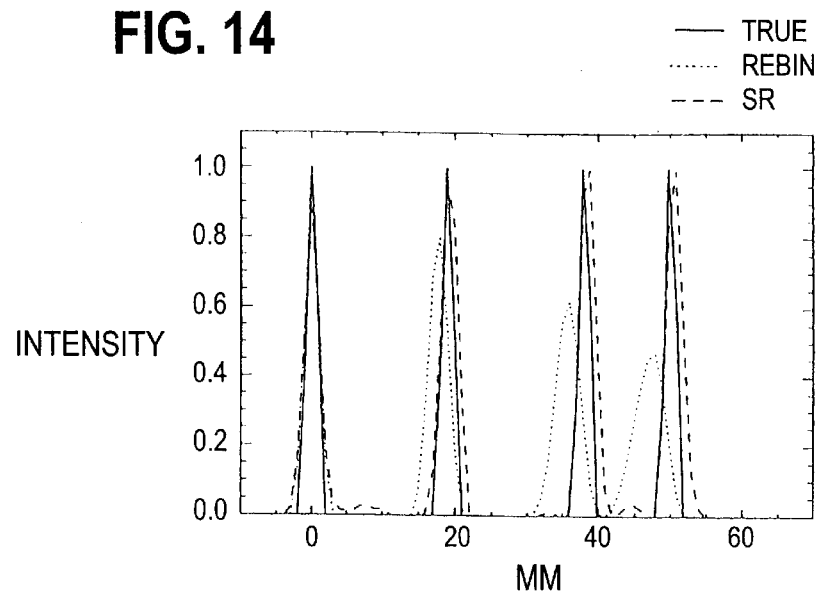
FIG. 14 depicts intensity profiles on the x-axis of the images, shown in FIGS. 11–13.

FIGS. 11–13 compares an actual. (i.e., a true) image with the reconstructed images obtained by REBIN and SR. FIG. 11 is the REBIN image, FIG. 12 is the true image and FIG. 13 is the SR image. Their profiles on the x-axis are shown in FIG. 14. From these profiles, the full-width-at-half-maximums (FWRMs) and peak positions for the four sources on the x-axis may be calculated. The results are shown in Table I. In the REBIN image, as the source moves closer to the edge of the FOV, its shape becomes more radially elongated, and its peak intensity becomes smaller. In addition, its apparent position as determined by the intensity peak shifts away from its actual location. In the SR image, these degradations are substantially reduced. The size and peak intensity of the source remains relatively constant, and its positioning is more accurate. As shown in Table I, the FWHM of the source increases by 123% at ~5 cm away from the center in the REBIN image. In contrast, in the SR image the variations of the FWHM are less than 23% within the FOV, corresponding to a factor of 5.3 improvement in resolution uniformity across the whole FOV. For a source 5 cm away from the center of the FOV, the resolution is improved by a factor of 2 from 5.04 mm to 2.47 mm. Also, the largest source mispositioning decreases from 2 mm in the REBIN image to, 1 mm in the SR image.

TABLE I

| TRUE | 1.83/0.00 | 1.83/18.92 | 1.88/37.85 | 1.88/49.80 |
| REBIN | 2.26/0.00 | 3.15/17.93 | 4.01/35.86 | 5.04/47.81 |
| SR | 2.27/0.00 | 2.79/18.92 | 2.53/38.84 | 2.47/50.80 |

The SR approach used by the system 10 produces very promising results for noiseless data by effectively removing parallax errors for sources in a FOV as large as 98% of the detector ring. In comparison with REBIN images, SR images have superior resolution uniformity, more accurate source positioning and better intensity recovery for sources away from the center of the FOV. In addition, the SR approach is computationally efficient. These properties make the described approach very promising for accurate image reconstruction of DOI-PET data in routine applications.

A specific embodiment of a method and apparatus for reconstructing images for DOI-PET systems according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A method of reconstructing images from data obtained from scintillation events occurring within a projection space of a depth-of-interaction positron emission tomography system, such method comprising the steps of:
   identifying a segment of each depth-of-interaction detector of respective pairs of depth-of-interaction detectors detecting the scintillation events of the data obtained within the projection space; and
   estimating a set of sinograms from the data based upon a set of depth-independent point spread functions of the identified segments of the respective pairs of depth-of-interaction detectors.

2. The method of reconstructing images as in claim 1 further comprising determining a line of coincidence joining the identified segments of each pair of depth-of-interaction detectors.

3. The method of reconstructing images as in claim 2 wherein the step of determining the line of coincidence further comprises identifying a point on a front face of each identified segment of each pair of depth-of-intersection detectors.

4. The method of reconstructing images as in claim 3 further comprising determining an angle φ and a position ρ of the line of coincidence within the projection space.

5. The method of reconstructing images as in claim 1 wherein the step of estimating the set of sinograms further comprises performing a sinogram restoration on the data.

6. The method of reconstructing images as in claim 1 wherein the step of estimating the set of sinograms further comprises solving a matrix equation relating the data obtained within the projection space at an angular view i to a system response matrix formed by a set of depth-independent point spread functions at angular view i.

7. The method of reconstructing images as in claim 6 wherein the step of estimating the matrix equation further comprises solving the matrix equation $p_i = E\{g_i\}H_i^{-1}$, where $p_i$ is the projection of the sinogram at angular view i, $E\{g_i\}$ is the data obtained within the projection space at angular view i and $H_i$ is the set of depth-independent point spread functions at angular view i.

8. The method of reconstructing images as in claim 7 wherein the step of solving the matrix equation further comprises using an expectation-maximization algorithm.

9. The method of reconstructing images as in claim 1 further comprising reconstructing an image from the estimated set of sinograms using a filtered backprojection algorithm.

10. The method of reconstructing images as in claim 1 wherein the step of identifying pairs of depth-of-interaction detectors further comprises temporally correlating an output of a plurality of crystals.

11. The method of reconstructing images as in claim 1 wherein the step of identifying a segment of each depth-of-interaction detector further comprises detecting an output signal from a photomultiplier tube associated with each depth of interaction detector.

12. The method of reconstructing images as in claim 11 wherein the step of detecting the output signal from the photomultiplier tube further comprises identifying the segment based upon a rate of rise of the output signal.

13. The method of reconstructing images as in claim 1 further comprising measuring a depth-independent point spread function for each pair of depth-of-interaction detectors.

14. The method of reconstructing images as in claim 1 wherein the step of estimating the set of sinograms further comprises using a Kalman filter.

15. Apparatus for reconstructing images from data obtained from scintillation events occurring within a projection space of a depth-of-interaction positron emission tomography system, such apparatus comprising:
- means for identifying a segment of each depth-of-interaction detector of respective pairs of depth-of-interaction detectors detecting the scintillation events of the data obtained within the projection space; and
- means for estimating a set of sinograms from the data based upon a set of depth-independent point spread functions of the identified segments of the respective pairs of depth-of-interaction detectors.

16. The apparatus for reconstructing images as in claim 15 further comprising means for determining a line of coincidence joining the identified segments of each pair of depth-of-interaction detectors.

17. The apparatus for reconstructing images as in claim 16 wherein the means for determining the line of coincidence further comprises means for identifying a point on a front face of each identified segment of each pair of depth-of-intersection detectors.

18. The apparatus for reconstructing images as in claim 17 further comprising means for determining an angle $\phi$ and a position $\rho$ of the line of coincidence within the projection space.

19. The apparatus for reconstructing images as in claim 15 wherein the means for estimating the set of sinograms further comprises means for performing a sinogram restoration on the data.

20. The apparatus for reconstructing images as in claim 19 wherein the means for estimating the set of sinograms further comprises means for solving a matrix equation relating the data obtained within the projection space at an angular view i to a system response matrix formed by a set of depth-independent point spread functions at angular view i.

21. The apparatus for reconstructing images as in claim 20 wherein the means for estimating the matrix equation further comprises means for solving the matrix equation $p_i = E\{g_i\} H_i^{-1}$, where $p_i$ is the projection of the sinogram at angular view i, $E\{g_i\}$ is the data obtained within the projection space at angular view i and $H_i$ is the set of depth-independent point spread functions at angular view i.

22. The apparatus for reconstructing images as in claim 21 wherein the means for solving the matrix equation further comprises means for using an expectation-maximization algorithm.

23. The apparatus for reconstructing images as in claim 15 further comprising means for reconstructing an image from the estimated set of sinograms using a filtered backprojection algorithm.

24. The apparatus for reconstructing images as in claim 15 wherein the means for identifying pairs of depth-of-interaction detectors further comprises means for temporally correlating an output of a plurality of crystals.

25. The apparatus for reconstructing images as in claim 15 wherein the means for identifying a segment of each depth-of-interaction detector further comprises means for detecting an output signal from a photomultiplier tube associated with each depth of interaction detector.

26. The apparatus for reconstructing images as in claim 25 wherein the means for detecting the output signal from the photomultiplier tube further comprises means for identifying the segment based upon a rate of rise of the output signal.

27. Apparatus for reconstructing images from data obtained from scintillation events occurring within a projection space of a depth-of-interaction positron emission tomography system, such apparatus comprising:
- a scintillation processor adapted to identify a segment of each depth-of-interaction detector of respective pairs of depth-of-interaction detectors detecting the scintillation events of the data obtained within the projection space; and
- a sinogram processor adapted to estimate a set of sinograms from the data based upon a set of depth-independent point spread functions of the identified segments of the respective pairs of depth-of-interaction detectors.

28. The apparatus for reconstructing images as in claim 27 further comprising a line processor adapted to determine a line of coincidence joining the identified segments of each pair of depth-of-interaction detectors.

29. The apparatus for reconstructing images as in claim 28 wherein the line processor further comprises a vector processor adapted to identify a point on a front face of each identified segment of each pair of depth-of-intersection detectors.

30. The apparatus for reconstructing images as in claim 29 further comprising an angle processor adapted to determine an angle $\phi$ and a position $\rho$ of the line of coincidence within the projection space.

31. The apparatus for reconstructing images as in claim 27 wherein the sinogram processor further comprises a restoration processor adapted to perform a sinogram restoration on the data.

32. The apparatus for reconstructing images as in claim 31 wherein the sinogram processor further comprises a matrix processor adapted to solve a matrix equation relating the data obtained within the projection space at an angular view i to a system response matrix formed by a set of depth-independent point spread functions at angular view i.

33. The apparatus for reconstructing images as in claim 32 wherein the matrix processor further comprises the matrix equation $p_i = E\{g_i\} H_i^{-1}$, where $p_i$ is the projection of the sinogram at angular view i, $E\{g_i\}$ is the data obtained within the projection space at angular view i and $H_i$ is the set of depth-independent point spread functions at angular view i.

34. The apparatus for reconstructing images as in claim 33 wherein the matrix processor further comprises an expectation-maximization algorithm.

35. The apparatus for reconstructing images as in claim 27 further comprising a backprojection processor adapted to reconstruct an image from the estimated set of sinograms using a filtered backprojection algorithm.

36. The apparatus for reconstructing images as in claim 27 wherein the scintillation processor further comprises a comparator adapted to temporally correlate an output of a plurality of depth-of-interaction detectors.

37. The apparatus for reconstructing images as in claim 27 wherein the scintillation processor further comprises a photomultiplier tube adapted to detect an output signal from each depth of interaction detector.

38. The apparatus for reconstructing images as in claim 37 wherein the photo-multiplier tube further comprises rate-of-rise detector adapted to identify the segment based upon a rate of rise of the output signal.

39. The apparatus for reconstructing images as in claim 27 further comprises a field of view at least 75% as large as a depth of interaction detector ring diameter.

40. A method of reconstruction images from data obtained from scintillation events occurring within a projection space of a depth-of-interaction positron emission tomography system, such method comprising the steps of:

identifying pairs of crystals detecting the scintillation events of the data obtained within the projection space;

determining a position of the pairs of crystals in the projection space;

estimating a set of sinograms from the data based upon a set of depth-independent point spread functions of the pairs of crystals at the determined positions.

41. The method of reconstructing images as in claim 40 further comprising reconstructing an image from the estimated set of sinograms using a filtered backprojection algorithm.

42. The method of reconstructing images as in claim 40 wherein the step of identifying pairs of crystals further comprising temporally correlating an output of a plurality of crystals.

43. The method of reconstructing images as in claim 40 wherein the step of determining a position of the pairs of crystals further comprises forming a line of coincidence between the paired crystals.

44. The method of reconstructing images as in claim 43 further comprising identifying a point spread function perpendicular to the line of coincidence.

45. The method of reconstructing images as in claim 40 wherein the step of estimating the set of sinograms further comprising solving the matrix equation $p_i = E\{g_i\} H_i^{-1}$, where $E\{g_i\}$ is the data obtained with the projection space at an angular view i and $H_i$ is the depth-independent point spread function and angular view i.

* * * * *

UNITED STATES PATENT AND TRADEMARK OFFICE
CERTIFICATE OF CORRECTION

| | | |
|---|---|---|
| PATENT NO. | : 6,528,793 B1 | |
| APPLICATION NO. | : 09/693478 | |
| DATED | : March 4, 2003 | |
| INVENTOR(S) | : Chen et al. | |

It is certified that error appears in the above-identified patent and that said Letters Patent is hereby corrected as shown below:

In Column 1 for the above-identified patent, please replace the first sentence after the title in the patent with the following sentence:

--"This invention was made with government support under grant number CA 70449 awarded by the National Institutes of Health (NIH). The government has certain rights in the invention."--

Signed and Sealed this

Twenty-first Day of August, 2007

JON W. DUDAS
*Director of the United States Patent and Trademark Office*